United States Patent [19]

Kaule et al.

[11] 4,169,662
[45] Oct. 2, 1979

[54] METHOD AND APPARATUS FOR PRODUCING ACOUSTIC WAVES BY LASER PULSES

[75] Inventors: Walter Kaule; Erik Primbsch, both of Cologne, Fed. Rep. of Germany

[73] Assignee: Krautkramer-Branson, Incorporated, Stratford, Conn.

[21] Appl. No.: 856,337

[22] Filed: Dec. 1, 1977

[30] Foreign Application Priority Data

Feb. 24, 1977 [DE] Fed. Rep. of Germany ....... 2707883

[51] Int. Cl.$^2$ ................................................ G02F 1/11
[52] U.S. Cl. .................................................... 350/358
[58] Field of Search .................... 219/121 L, 121 LM; 350/358; 331/94.5 N, DIG. 1

[56] References Cited

U.S. PATENT DOCUMENTS 3,710,283  1/1973  Alphonse ............................ 350/358

*Primary Examiner*—William L. Sikes
*Attorney, Agent, or Firm*—Ervin B. Steinberg; Philip J. Feig

[57] ABSTRACT

Focussed acoustic waves are generated free of physical contact in a light absorbing workpiece by the use of laser beam means providing a coherent light beam which in a pulsed manner impinges upon the surface of the workpiece in a Fresnel zone pattern. The zoned pattern is caused in a typical example by a suitable mask interposed between the laser source and workpiece surface. The thermal effect responsive to the laser beam energy produces in the workpiece a plurality of acoustic waves having a common focal point.

12 Claims, 3 Drawing Figures

METHOD AND APPARATUS FOR PRODUCING ACOUSTIC WAVES BY LASER PULSES

BRIEF SUMMARY OF THE INVENTION

This invention concerns a method and apparatus for producing without physical contact focussed acoustic waves in light absorbing workpieces for use in the non-destructive testing of such workpieces by ultrasonic energy. The ultrasonic wave is generated responsive to thermal effects at the surface of the workpiece.

The generation of an acoustic wave in a light absorbing workpiece is known and described, for instance, in "Werkstoffprufung mit Ultraschall" (book) by J. & H. Krautkramer, 3rd edition (1975) Springer Verlag, Berlin and Heidelberg, pages 148 to 150. The surface of a workpiece is illuminated with coherent light pulses from a laser source and such light pulses are absorbed by the surface, causing a localized heating which, in turn, generates mechanical stress in the material structure. The mechanical stresses propagate as an elastic wave (acoustic wave) into the interior of the workpiece. The conditions necessary for such an effect are: The pulse duration of the laser beam must be short in relation to the period of the acoustic wave, and the absorption of the laser beam pulse energy must occur at the workpiece surface, that is, the depth of penetration of the coherent light beam must be negligibly small in relation to the wavelength of the acoustic wave produced. For the described thermal method of producing an acoustic wave, the direction of propagation of the sound wave is always perpendicular to the workpiece surface. On account of the large difference between the velocity of light and that of the acoustic wave, a laser beam arrangement which is disposed at an oblique angle to the workpiece surface also produces an acoustic wave propagated only normal to the workpiece surface. Therefore, using the described simple arrangement the generation of a focussed acoustic wave is not possible. Known methods permit laser beams to be transmitted over a large distance to produce acoustic waves in remote workpieces, thereby making this method applicable to workpieces with hidden surfaces or workpieces having hot surfaces.

A primary purpose of this invention is the provision of means for producing free of physical contact a focussed acoustic beam on the surface of a workpiece by combining the known interference phenomenon and the propagation of fundamental waves known from the Huygen's principle.

In accordance with the invention described hereafter, laser beam pulses are transmitted to annular surface portions arranged in a Fresnel lens zone pattern for generating focussed ultrasonic waves. The fundamental waves propagated from the individual zones produce by virtue of interference a resultant spherical wave front which runs toward the center of curvature of the wave front.

When testing workpieces to which access with ultrasonic energy is difficult, it is necessary to produce acoustic pulses on the workpiece surfaces disposed at greater distances which may range from a few centimeters to several meters. On account of the great acoustic impedance difference between the workpiece and the surrounding medium (usually air) it is not possible to use a conventional ultrasonic test probe. The problems presented by the impedance mismatch can be avoided, however, when the workpiece surface itself is used as acoustic wave transmitter and if the energy conversion is structured in a manner that by virtue of interferences, directional propagation characteristics are imparted to the acoustic waves so derived. An acoustic wave and the ability to focus it toward a focal point is advantageous when the image of a defect is to be formed, in which case a point-like resolution using a sharply focussed acoustic beam becomes a necessity. The focussed beam then is swept over the defect in a scanning raster. A focussed beam will be found advantageous also for transmitting the highest available energy to a defect to be detected and, thus, for increasing the sensitivity of the test method.

In the present invention, instead of illuminating the workpiece surface uniformly, the surface portion which is to be excited with a focussed acoustic wave is illuminated in a Fresnel zone pattern. Responsive to the thermal effect acoustic waves are generated at the illuminated portions and such waves mutually interfere and propagate in the form of spherically curved wave fronts. The wave fronts have a common center which forms the focal point of the acoustic wave.

If the Fresnel zones are generated simultaneously by a modulated laser beam pulse, an acoustic wave is produced consisting of several wave trains. In the event that the zones are generated in sequence, it is possible to produce a single wave train (shock wave).

For a better understanding of the present invention, reference is made to the following specification in conjunction with the accompanying drawings.

DETAILED DESCRIPTION OF THE INVENTION

As used herein the term "illuminating in a pattern" or a similar expression shall mean that coherent light in accordance with the invention illuminates predetermined workpiece surface portions in order to produce acoustic waves in response to the thermal effect occurring at the illuminated portions.

Figure 1:
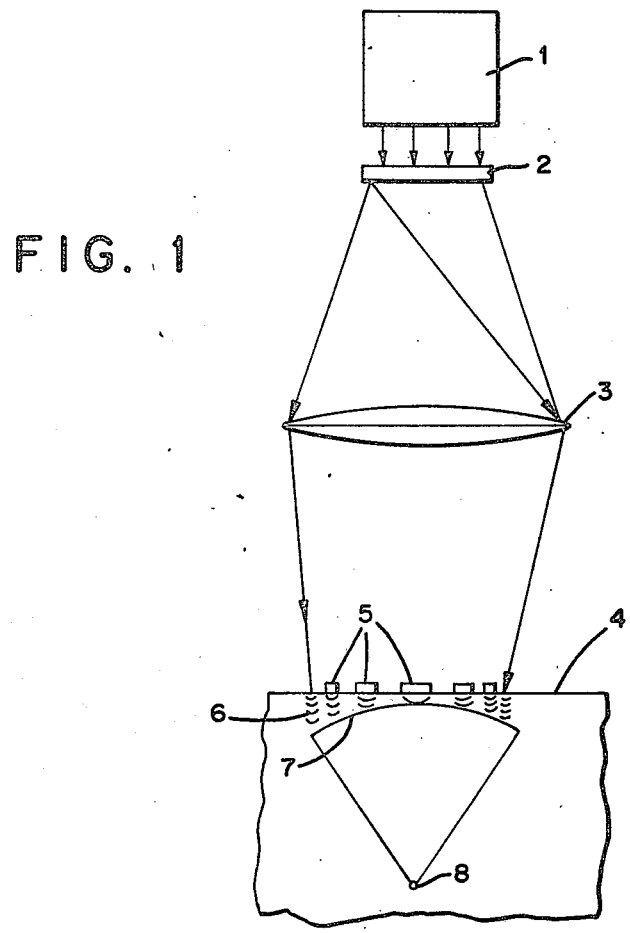
FIG. 1 is a schematic side view of the laser beam arrangement and workpiece including a diagram tracing the path of the light waves and acoustic waves.

Referring now to the figures and FIG. 1 in particular, the laser source 1 sends a beam of coherent light toward the zone mask 2. The pattern of the zone mask 2 is imaged by the condensing lens 3 on the workpiece surface 4. As a result, the workpiece surface is illuminated in a pattern of Fresnel zones 5. The zones for the sake of clarity of presentation are shown raised in the figure. Fundamental acoustic waves 6 are propagated from the illuminated zones and such waves propagate to yield a resultant spherical wave front 7 in accordance with known physical laws. The wave front 7 has the point 8 as its center which also forms the focal point. The wave produced comprises at least as many wave fronts as there are illuminated zones.

In a modification of the above stated arrangement, the zone mask 2 can be disposed directly upon the workpiece surface and thereby shade the workpiece surface areas which are not to be illuminated by the laser beam.

Figure 3:
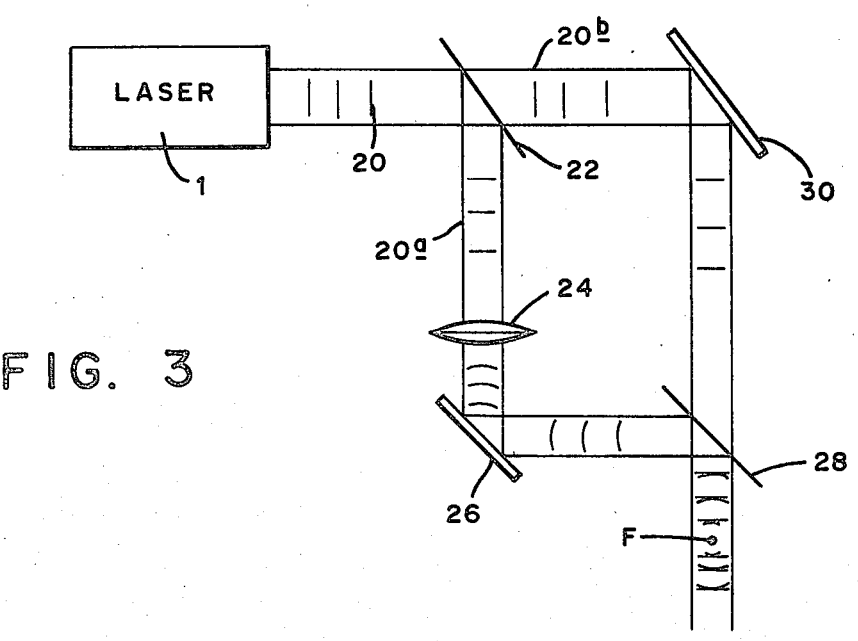
FIG. 3 is a further modification showing the use of optical interference for causing a zone pattern.

Another modification as shown in FIG. 3 comprises dividing the laser beam into two coherent beam portions and producing a zonal pattern by means of interference between the recombined beam portions. Referring to this figure, the beam of laser light 20 produced by the laser 1 is divided by a beam splitter 22 into a first beam portion 20a and a second portion 20b. Light beam portion 20a is passed through a condensing lens 24, reflected at a mirror 26 and is reflected once more at a transparent mirror 28. Light portion 20b is reflected at mirror 30, passed through transparent mirror 28 and combined with beam portion 20a. The result is a zone pattern produced by the superposing of the spherical waves passing through lens 24 with the plane waves of beam portion 20b.

Figure 2:
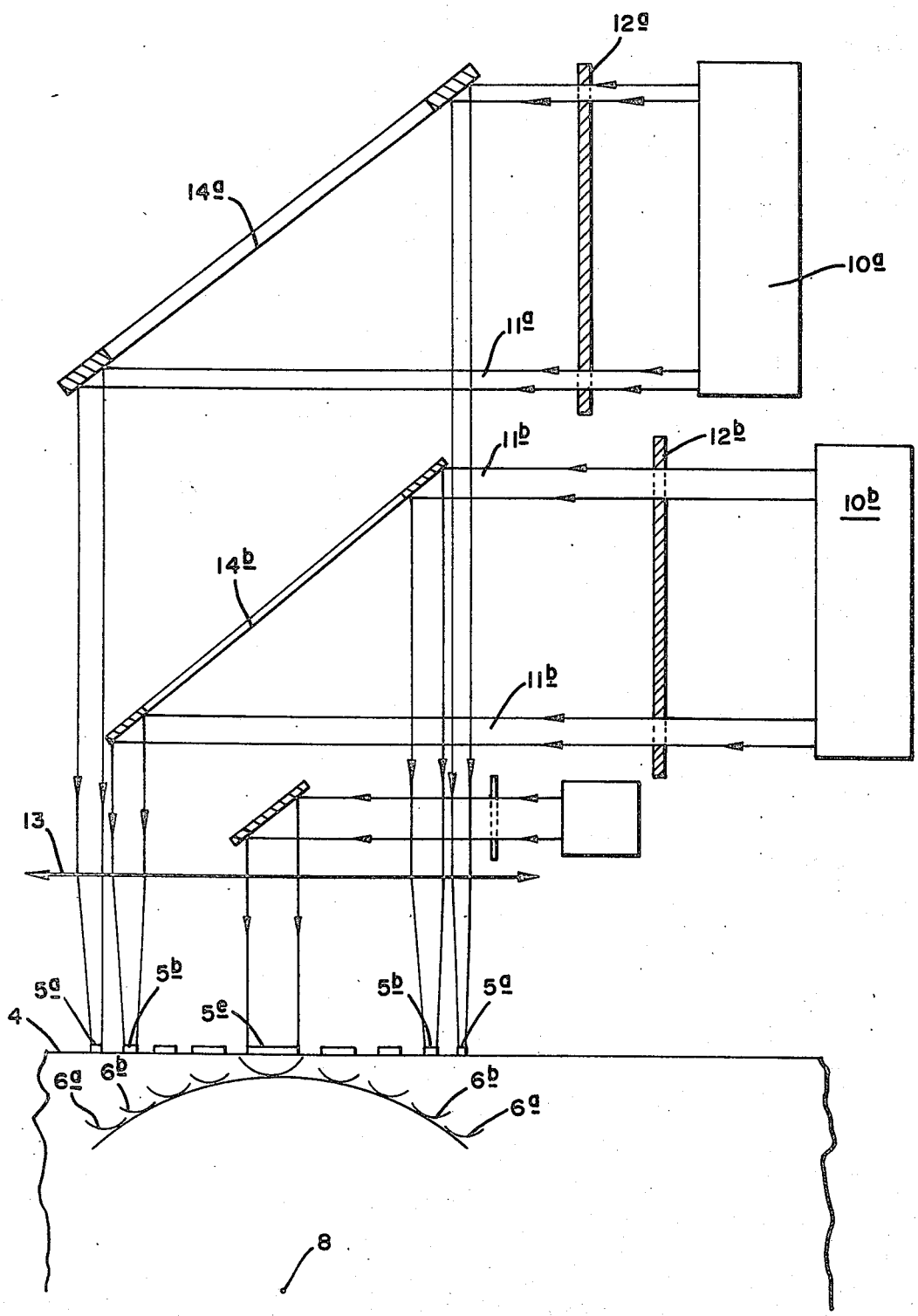
FIG. 2 is a modification of the arrangement per FIG. 1 showing the sequential operation of a plurality of laser sources.

A further modification comprises an arrangement wherein the zones are not illuminated simultaneously, but provision is made for the predetermined sequential illumination of the zones from the outer region inward, as indicated in FIG. 2. Such an arrangement is particularly advantageous when the acoustic wave does not consist of several wave trains, but it is desired that a shock wave be produced.

The beam of coherent light 11a produced by laser source 10a is transmitted through apertures in a zone mask 12a from where the non-intercepted beam portion reaches the inclined mirror 14a. The beam is reflected thereat toward the condensing lens 13 and impinges upon the workpiece surface 4 to provide an illuminated annular zone 5a. Responsive to the thermal effect, a fundamental wave 6a is produced. Somewhat later in time, the time delay being defined by the physical laws pertaining to the construction of Fresnel zones, laser source 10b is activated. The coherent light beam is intercepted by the apertured zone mask 12b and the non-intercepted beam portion is deflected by mirror 14b and impinges via condensing lens 13 upon the workpiece surface 4 to provide an illuminated annular zone 5b. The resulting thermal effect causes a fundamental wave 6b propagated from the zone 5b. Further laser beam sources are used for producing additional Fresnel zones toward the center until lastly the zone designated as 5e is generated. The resulting acoustic wave front is focussed toward the point 8.

The operation of the laser sources in timed sequence is dependent upon the diameter of the Fresnel zones, the focal length desired, the quantity of zones, and the velocity of the acoustic wave. The physical principle for this determination is explained in "Einfuhrung in die Theoretische Physik" (book) by Clemens Schaefer, 3rd volume, Section 1, pages 585 et seq., Verlag Walter de Gruyter, Berlin (Germany) 1932.

In accordance with the method and apparatus described above focussed acoustic waves can be produced in a workpiece, particularly shock waves, for determining and locating defects, for instance, in a metallic workpiece, without the need for direct physical contact between the source of energy generating the acoustic wave and the workpiece.

What is claimed is:

1. Method for producing free of physical contact on the surface of a light absorbing workpiece an ultrasonic wave useful for nondestructively testing such workpiece by ultrasonic energy comprising:
   disposing a laser source adapted to produce a beam of coherent light for illuminating a workpiece surface;
   causing said source to illuminate portions on the workpiece surface with coherent light pulses in a Fresnel zone pattern,
   whereby the coherent light pulses responsive to the thermal effect manifest in the workpiece generate fundamental ultrasonic waves which propagate from the respective zones and provide a resultant spherical wave front propagating toward a central focal point.

2. Method for producing free of physical contact on the surface of a light absorbing workpiece an ultrasonic wave as set forth in claim 1, causing said coherent light pulses to illuminate said portions in such a manner that individual annular portions are illuminated in timed sequence to provide a resultant wave front having a focal point.

3. Method for producing free of physical contact on the surface of a light absorbing workpiece an ultrasonic wave as set forth in claim 1, said portions being of annular shape and being illuminated substantially simultaneously.

4. Method for producing free of physical contact on the surface of a light absorbing workpiece an ultrasonic wave as set forth in claim 1, said portions forming a Fresnel zone pattern being produced by disposing apertured zone mask means in the path of said coherent light.

5. Method for producing free of physical contact on the surface of a light absorbing workpiece an ultrasonic wave as set forth in claim 1, said portions forming a Fresnel zone pattern being produced by disposing lens means and apertured zone mask means in the path of said coherent light.

6. Method for producing free of physical contact on the surface of a light absorbing workpiece an ultrasonic wave as set forth in claim 1, said source providing a pair of coherent beam portions which by interference are caused to form said Fresnel zone pattern on said workpiece surface.

7. An apparatus for producing free of physical contact on the surface of a light absorbing workpiece an ultrasonic wave useful for nondestructively testing such workpiece by ultrasonic energy comprising:
   laser source means for providing a pulsed beam of coherent light disposed for illuminating the surface of a workpiece;
   means disposed in the path of said beam for causing the surface of the workpiece to be illuminated in a pattern of annular surface portions forming a Fresnel zone,
   whereby responsive to such pulsed illumination the respective annular portions are subjected to a thermal effect which causes a respective fundamental ultrasonic wave propagating from each such portion and the respective ultrasonic waves by interference produce a resultant spherical wave front propagating toward a central focal point.

8. An apparatus for producing free of physical contact on the surface of a light absorbing workpiece an ultrasonic wave as set forth in claim 7, said laser means comprising a plurality of laser means, each laser means disposed for illuminating a predetermined annular surface portion, and means coupled to said laser means for causing said annular surface portions to be energized in timed sequence to provide a resultant ultrasonic wave front having a focal point.

9. An apparatus for producing free of physical contact on the surface of a light absorbing workpiece an ultrasonic wave as set forth in claim 7, said laser source means illuminating said surface portions substantially simultaneously.

10. An apparatus for producing free of physical contact on the surface of a light absorbing workpiece an ultrasonic wave as set forth in claim 7, said means disposed in the path of said beam comprising aperture mask means.

11. An apparatus for producing free of physical contact on the surface of a light absorbing workpiece an ultrasonic wave as set forth in claim 7, said means disposed in the path of said beam comprising apertured zone mask means and lens means.

12. An apparatus for producing free of physical contact on the surface of a light absorbing workpiece an ultrasonic wave as set forth in claim 7, said means disposed in the path of said beam comprising beam splitting means for providing a first laser beam portion comprising spherical waves and a second laser beam portion comprising plane waves, and means for superposing said respective wave portions.

* * * * *